United States Patent
Reavill

(10) Patent No.: US 8,029,481 B2
(45) Date of Patent: Oct. 4, 2011

(54) APPARATUS AND METHOD OF INSERTING AN INFUSING CATHETER AND DETERMINING CATHETER DEPTH WITHOUT A GUIDEWIRE OR DIRECT CONTACT WITH THE CATHETER

(76) Inventor: Matthew Dickson Reavill, Plainfield, IL (US)

( * ) Notice: Subject to any disclaimer, the term of this patent is extended or adjusted under 35 U.S.C. 154(b) by 293 days.

(21) Appl. No.: 11/550,206

(22) Filed: Oct. 17, 2006

(65) Prior Publication Data
US 2008/0091137 A1 Apr. 17, 2008

(51) Int. Cl.
*A61M 25/00* (2006.01)
*A61M 5/178* (2006.01)

(52) U.S. Cl. .............. 604/284; 604/164.04; 604/164.05; 604/171

(58) Field of Classification Search .......... 604/158–164, 604/27, 103.04, 171, 284
See application file for complete search history.

(56) References Cited

U.S. PATENT DOCUMENTS

| | | | |
|---|---|---|---|
| 3,786,810 A | 1/1974 | Pannier, Jr. et al. | |
| 4,397,091 A | 8/1983 | Gustavsson et al. | |
| 4,563,176 A | 1/1986 | Gustavsson et al. | |
| 5,195,978 A | 3/1993 | Schiffer | |
| 5,352,215 A | 10/1994 | Thome et al. | |
| 5,687,727 A | 11/1997 | Kraus et al. | |
| 6,077,250 A | 6/2000 | Snow et al. | |
| 6,086,008 A | 7/2000 | Gray et al. | |
| 6,517,520 B2 | 2/2003 | Chang et al. | |
| 7,048,719 B1 | 5/2006 | Monetti | |
| 7,172,580 B2 | 2/2007 | Hruska et al. | |
| 2003/0130620 A1 | 7/2003 | Alokaili | |
| 2006/0015068 A1 | 1/2006 | Amisar et al. | |

FOREIGN PATENT DOCUMENTS

| | | |
|---|---|---|
| EP | 0 226 397 | 6/1987 |
| EP | 1 245 191 | 10/2002 |
| EP | 1 512 427 | 3/2005 |
| WO | WO 93/14804 | 8/1993 |

*Primary Examiner* — Theodore J Stigell
*Assistant Examiner* — Imani Hayman
(74) *Attorney, Agent, or Firm* — Nixon & Vanderhye P.C.

(57) ABSTRACT

A catheter enables measuring and approximating its distal end position within the body to facilitate catheter insertion and improve accuracy and control. By wrapping a long infusion catheter with an outer coating, the catheter can be guided into a vein or vessel by pulling on the outer coating and forcing its separation in a Y-shaped separation housing anchored close to the insertion point. Since there is no need for a guidewire or stylet and the outer coating acts as a sterile peel package, the catheter can be placed while infusing and maintain its own closed sterile environment during insertion.

13 Claims, 4 Drawing Sheets

APPARATUS AND METHOD OF INSERTING AN INFUSING CATHETER AND DETERMINING CATHETER DEPTH WITHOUT A GUIDEWIRE OR DIRECT CONTACT WITH THE CATHETER

TECHNICAL FIELD

The present invention relates to methods and devices designed for controlling the movement of catheters useful in many medical procedures. In particular, an apparatus and method to facilitate a simple, closed, measurable insertion of a catheter without the need of a guidewire or stylet is disclosed.

BACKGROUND ART

Long catheters are commonly introduced into blood and other vessels during numerous medical procedures. In some procedures, accurate placement within vessels is important and desirable. Generally, guidewires are first inserted into the vessel so that the distal end of the guidewire is at the desired position to be treated. Catheters are provided with a suitable lumen into which the proximal guidewire end is inserted and the catheter is slid over the guidewire or stylet to the desired position.

In addition to difficulties associated with accurate, reproducible catheter placement, handling and manipulation of the catheters in an operating room environment can become unwieldy. Guidewires can create confusion about their use and may be a potential source of contamination during insertion. The need for maintaining sterility and verifying catheter placement is of concern. Of particular emphasis for this product is its application in emergency medicine where catheters need to be inserted quickly to begin therapies. Since there is less time in this environment, simpler more intuitive devices are favored, This environment also puts less emphasis on and has less capability of accommodating a sterile technique during insertion. Lastly this emergency environment often needs to maintain an infusion of fluid medications even before a long catheter is inserted into its final position.

SUMMARY

A long infusion catheter is surrounded by an outer coating that is not adhered to the catheter but does form a tight friction fit along its length that does not allow the catheter inside to slide within the coating and also protects the catheter sterile surface. The distal end of this arrangement has been arranged within a Y-shaped separation housing such that the coating splits away from the catheter and exits a coating exit of the Y-shaped housing and the catheter exits a separate catheter exit. Then by pulling on the coating exiting the coating exit of the Y-shaped housing, the catheter with the coating is drawn into the Y-shaped housing, separated from the coating, and propelled through the catheter exit. The catheter exit is connected to an introducer catheter to facilitate passage of the catheter into the vessel.

The coating serves additional purposes of preventing contamination to the catheter before separation and providing measurements about the inserted portion of the catheter by indicia printed on the coating. Measurements are also provided by using the separated coating length to trace the path of insertion and thereby approximate the distal end position of the catheter. The Y-shaped housing not only separates the coating from the catheter and allows for the propulsion of the catheter, the housing also insulates the catheter after separation from the coating by enclosing the exposed area of the catheter before it enters the introducer catheter. Since there is no guidewire needed for insertion, the long catheter can infuse fluids during insertion while determining position and/or final placement.

DESCRIPTION OF EXEMPLARY EMBODIMENTS

Figure 1:
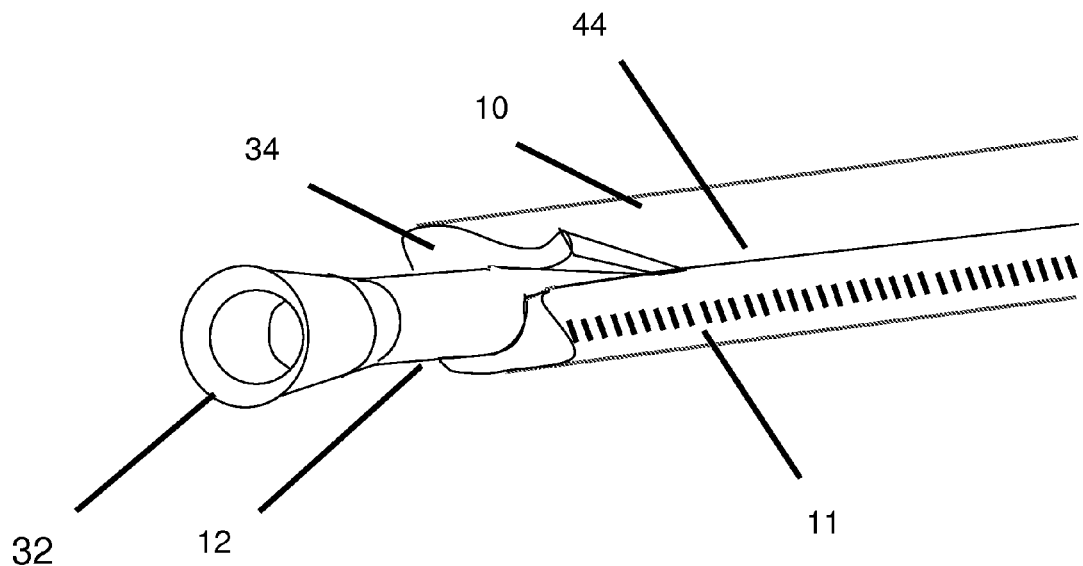
FIG. 1 is a perspective view illustrating a common long catheter that is jacketed along its entire length with a separable coating.
Figure 2:
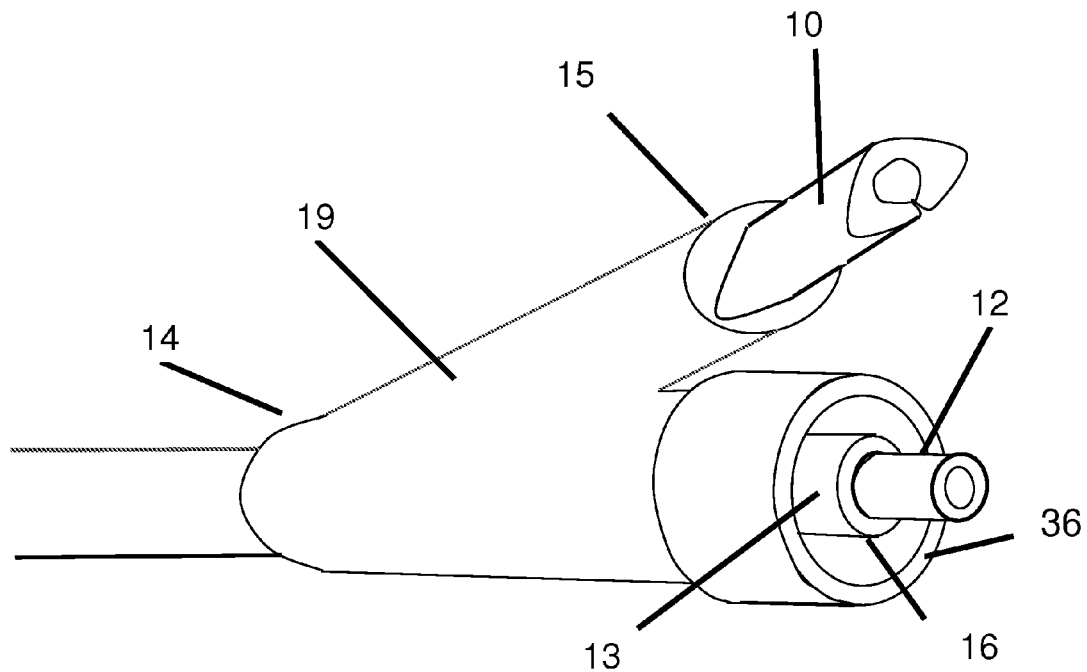
FIG. 2 is a perspective view of a Y-shaped housing that is used to separate the coating from the catheter and to enable the simple propulsion of the long catheter.
Figure 3:
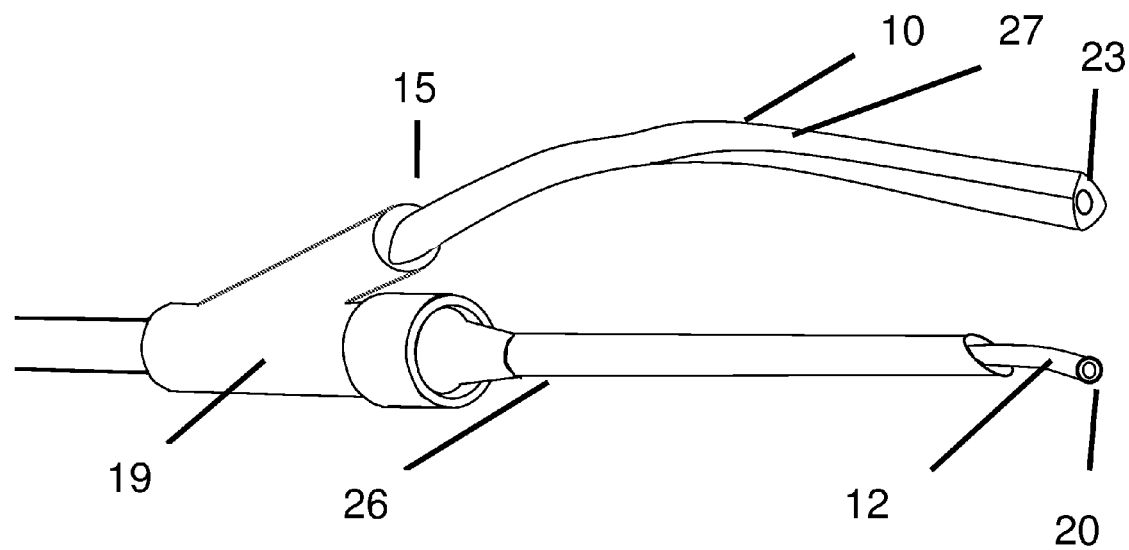
FIG. 3 is a perspective view of an embodiment of the invention with the "Y" shaped housing connected to an introducer catheter which shows that the catheter and separated coating are the same distance from the "Y" shaped housing, allowing the distal end of the separated coating to be used to approximate the distal end of the placed catheter by laying the coating over the expected path of the catheter.

In an exemplary embodiment, the apparatus includes a long coating 10, that has been fitted over a long catheter 12, as shown in FIG. 1 (often called a PICC Line) of the same length. The coating 10 is proportionally fitted and not adhered to the catheter and peels away easily. The coating is more flexible and pliant than the catheter 12, A Y-shaped housing 19, generally shown in FIG. 2, is provided with one entrance 14, and two exits, including a coating exit 15 and a catheter exit 16. The entrance lumen extends generally directly through to the catheter exit 16, possibly changing lumen size at or near the point where the coating 10 is removed from the catheter 12. The coating exit 15 leaves the housing 19 at an acute angle from the catheter exit 16. The lumen of the entrance is such that it will accommodate the coating-wrapped catheter. The lumen of the catheter exit 16 will accommodate the catheter, and the lumen of the coating exit 15 will accommodate the coating. When the coating-wrapped catheter, again shown in FIG. 2, is drawn into the entrance of the Y-shaped housing, by drawing the coating 10 out through the coating exit 15, the long catheter 12 inside the coating 10 is also carried into and through the Y-shaped housing 19. The catheter 12 separates from the coating 10 within the Y-shaped housing 19 and is channeled to the catheter exit 16 as it is propelled forward. The catheter exit 16 has a luer lock connector 36 and is connected to an introducer catheter 26, or equivalent, as shown in FIG. 3. The catheter is thereby guided through the introducer catheter 26 into the vessel where the introducer catheter 26 is located.

By preventing sterile surfaces from contacting non-sterile surfaces, the device and method described herein preserve the sterility of the catheter portion which is to be inserted into the vessel. Additional prevention of contamination is achieved by flexible air/fluid seals attached to the entrance 14, catheter exit 16 and coating exit 15 of the Y-shaped housing 19 that seal off clearance gaps between the Y-shaped housing 19 and the catheter 12 or coating 10 traveling within. The seals hold the catheter 12 and coating 10 in place thereby also functioning as brakes when the catheter 12 is not being advanced. This preservation of sterility for surfaces that have yet to be inserted, combined with the braking ability of the separation housing 19 on the catheter 12, allow intermittent insertion of the catheter 12 into the vessel. The catheter 12 can be held in place for an indefinite period of time, then advanced further into the vessel at a later time by pulling out an additional length of coating 10 from the Y-shaped housing 19. An example of utilizing this method is to insert the catheter 12 into vessel a small amount and infusing to achieve hydration and therefore increase overall vessel size. At a later time, after the vessel has increased in size due to the hydration, the catheter 12 can be advanced mid length into the vessel to facilitate infusions that require greater flow. Once diagnostic apparatus are in place to detect and determine final distal end position, the catheter 12 may be advanced further to the final insertion depth. At this point, the catheter 12 may remain in the Y-shaped housing 19 or be cut, refitted with a connector and anchored in place with a permanent securing device.

Figure 7:
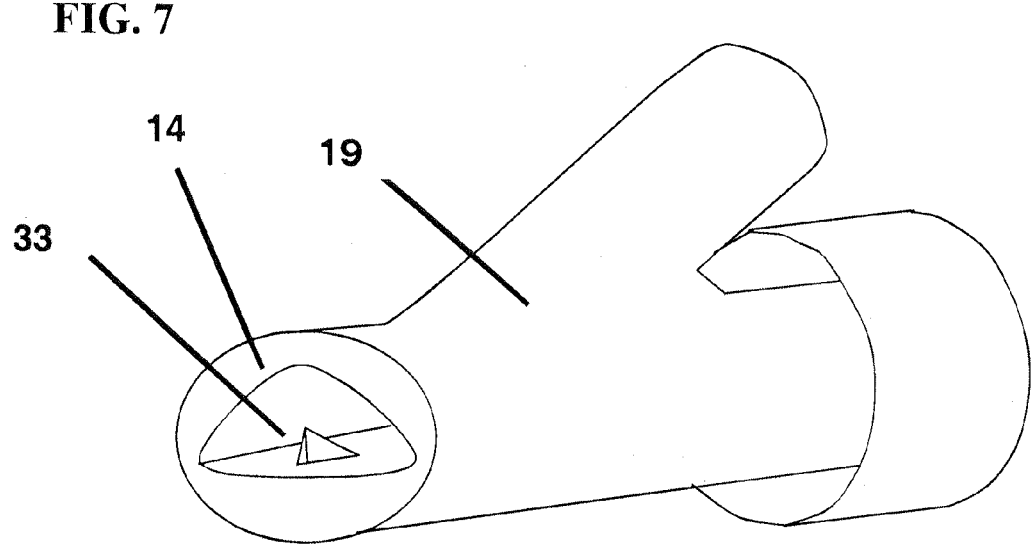
FIG. 7 is a perspective view illustrating the entrance of the Y-shaped housing with a blade located in the entrance of the housing.

The coating 10, shown in FIG. 1, will have an oval, shaped or grooved outer profile 34 that aligns with a corresponding oval, shaped or grooved profile at the entrance of the Y-shaped housing 14 as shown in FIG. 7. This will align the slit 44 in the coating 10 within the Y-shaped housing 19 to facilitate peeling away the coating by the Y-shaped housing 19.

The apparatus and method described herein provide the ability to infuse through the catheter 12 during insertion. Fluid exiting the distal end of the catheter 12 can facilitate insertion by providing axial movement of the distal end of the catheter 12, keeping it away from the vessel walls, thus facilitating passage within the vessel as it moves forward.

The catheter may also be filled or primed with detectable media to enhance its appearance when viewed with external diagnostic equipment such as but not limited to x-ray.

Numbered indicia printed on the exterior of the coating 10, again shown in FIG. 3, facilitates a method of measurement where the insertion depth is measured by reading the indicia where the coating exits the coating exit 15 of the Y-shaped housing 19. Dual indicia can be utilized. The first set of numbered indicia increases from a low number at the distal end 23 of the coating 10 to higher readings at the proximal end of the coating 10. Reading these indicia at the coating exit 15 indicates insertion depth of the catheter 12. A second set of indicia increases from the proximal end to the distal end 23 of the coating 10. Reading these indicia at the coating exit 15 allows the determination of the amount of catheter available for insertion.

The arrangement provides a method of catheter distal end point approximation, shown in FIG. 3, by utilizing the drawn length 27 of coating 10 that has exited the Y-shaped housing 19. The drawn coating length 27 is placed above the intended path of the catheter 12 within the vessel. Since the exiting catheter and exiting coating are equidistant from the Y-shaped housing 19, the distal end 23 of the coating 10 would be directly above the distal end of the catheter 20 within the vessel using this method.

Ultrasound or other noninvasive diagnostic methods are often used during catheter insertion to visualize position or placement of a catheter being inserted within the vessel. Technicians often maneuver a wand or hand held type detector above the area to be viewed. By attaching a connector to the distal end 23 of the coating 10 and affixing the connector to the wand or hand held device, the catheter 12 may be advanced while simultaneously observing the distal end of the catheter 12 in the vessel as it progresses forward.

Other catheter distal end detection methods utilize electronic or magnetic communication between a wire or electrical conduit within the lumen of the inserted catheter and an external detector located above the anticipated location of the wire/electrical conduit distal end within the catheter. The arrangement described herein could provide assistance to these types of detection by incorporating wire or electrical conduit within the coating itself to facilitate communication between the inserted wire/electrical conduit and the detection device.

Figure 4:
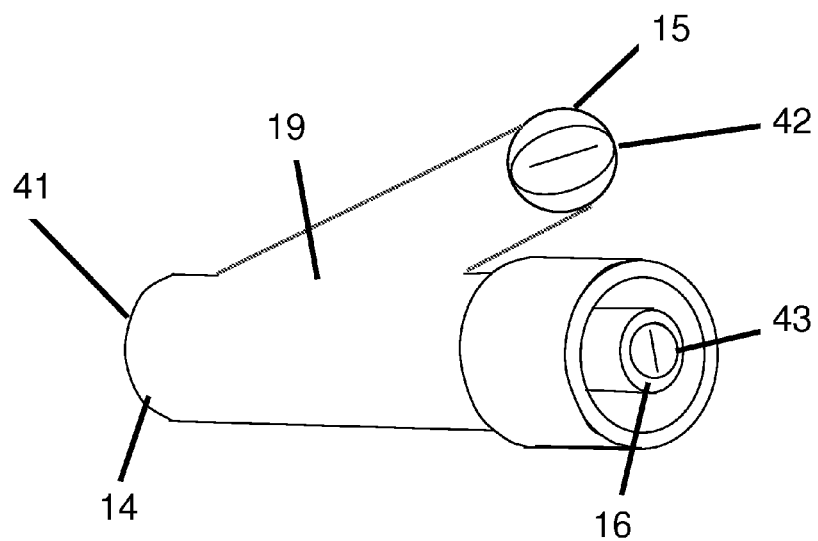
FIG. 4 is a perspective view illustrating flexible air/fluid seals at the entrance and exits of the Y-shaped housing.
Figure 5:
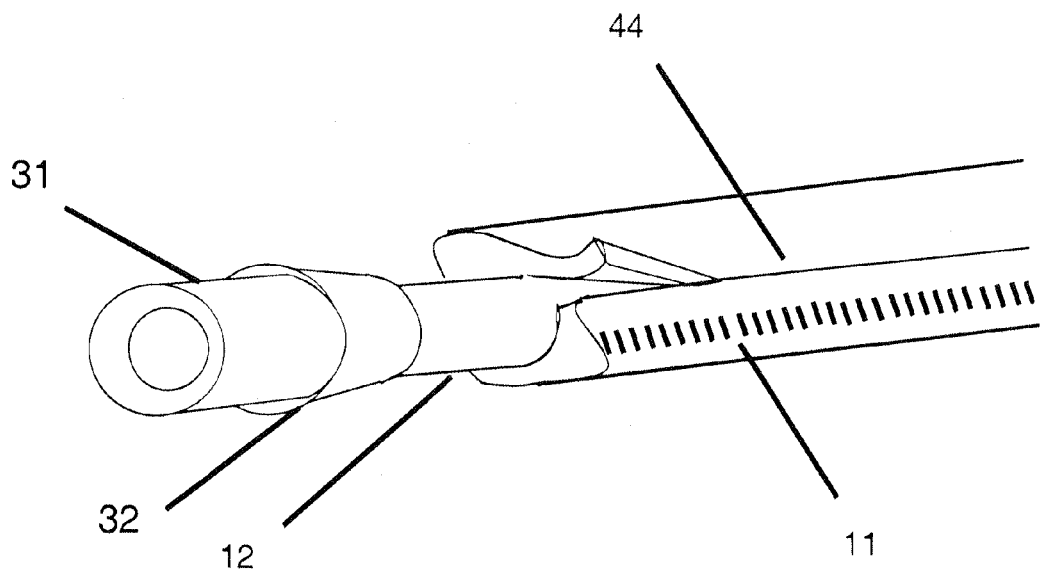
FIG. 5 is a perspective view illustrating an end cap attached to the female luer connector at the proximal end of the catheter.

The coating 10 before separation within the Y-shaped housing 19 protects the surface of the long catheter 12 from contact contamination. The only area where the catheter 12 becomes exposed is inside the "Y" shaped housing 19 at the point where separation occurs until the point it exits the catheter exit 16 of the "Y" shaped housing 19. To prevent contamination to the exposed catheter, the "Y" shaped housing 19 also seals out air and fluid. To accomplish this, the interior of the "Y" shaped housing 19 is completely enclosed and is fitted with flexible air/fluid seals at the entrance 14, as shown in FIG. 4, the coating exit 15 and the catheter exit 16. These flexible air/fluid seals are affixed to the "Y" shape housing 19 and conform to the outer surface of the catheter 12 or coating 10 that travels within to seal out air/fluid and still allow the catheter 12 or coating 10 to pass. By attaching an end cap 31, as shown in FIG. 5, and/or an infusion source to the female luer 32 at the proximal end of the catheter 12, the apparatus becomes a closed method of insertion.

In FIG. 4, on the Y-shaped housing 19, the entrance seal 41 at entrance 14, the catheter seal 43 at catheter exit 16, and coating seal 42 at coating exit 15 of the Y-shaped housing 19 further facilitate a unique feature of the arrangement by holding the catheter 12 in place within the vessel when the catheter is not being advanced. This arrangement ensures the catheter does not change depth unless the coating 10 is advanced through the Y-shaped housing 19. Combined with the closed method of insertion detailed above, intermittent levels of insertion are available without the risk of the catheter 12 changing depth and becoming contaminated.

Figure 8:
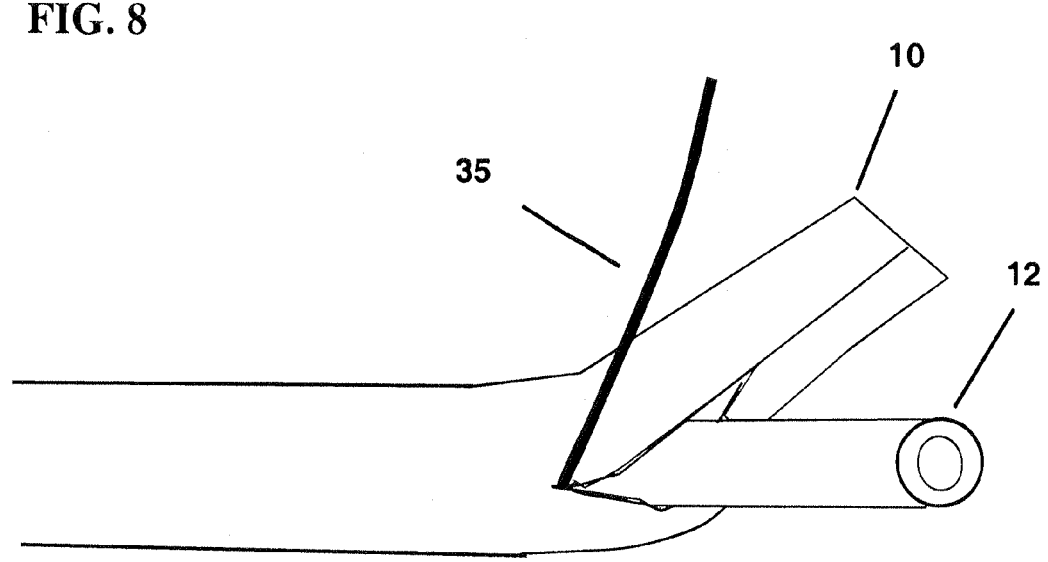
FIG. 8 is a perspective view illustrating a wire between the coating and catheter used to split the coating.

Separation of the coating 10 from the catheter 12 inside the Y-shaped housing 19 can be accomplished in a variety of ways. The first method is to have a slit that runs along the entire length of the coating 10, thus allowing the coating 10 to be pulled or peeled away at an angle and out the coating exit 15 of the Y-shaped housing 19. Since the catheter 12 is more rigid than the coating 10, the catheter 12 cannot make the same bend as the coating 10 and is propelled out the catheter exit 16. Another method of splitting and separating the coating 10 is to attach a knife edge or blade 33, as shown in FIG. 7, inside the Y-shaped housing 19 situated so that it slits the coating 10 only as it passes through the Y-shaped housing 19 and does not split the catheter 12 inside the coating 10. Separation occurs as in the pre-split method detailed above. A third method is to incorporate a cutting wire 35, shown in FIG. 8, or band between the catheter 12 and the coating 10 that splits the coating 10 as it is pulled out the coating exit 15 of the Y-shaped housing 19, then separation occurs as described above. Another method to split the coating 10 and achieve separation within the Y-shaped housing 19 is to incorporate a seam of thinner material or a perforation into the coating wall.

As the coating 10 is pulled to its coating exit 15 at an angle, and the catheter 12 cannot bend as it continues to the catheter exit 16, a tear occurs in the coating 10 at this seam or perforation. Still another method is to incorporate a runner or band of material manufactured so that it is attached to the length of the catheter 12 so that the catheter 12 and the runner or band are of the same material and are one piece. The runner or band would separate from the catheter 12 and propel the catheter 12 out the catheter exit 16, as the runner or band is pulled out of the coating exit 15 of the Y-shaped housing 19.

Figure 6:
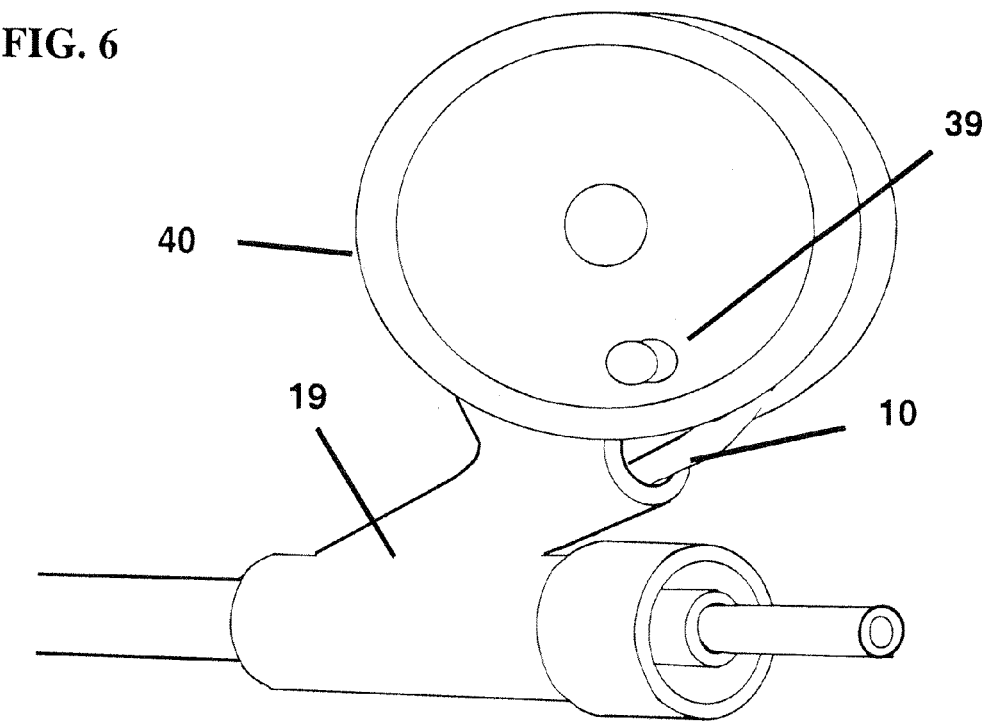
FIG. 6 is a perspective view illustrating a reel attached to the Y-shaped housing that mechanically draws the coating through the Y-shaped housing when the reel is turned.

The Y-shaped housing 19 could be fitted with a take-up reel 40 for the coating 10 in which turning a knob 39 on the take up reel 40 as shown in FIG. 6 would mechanically draw the coating 10 through the Y-shaped housing 19.

The present invention is more intuitive and facilitates quicker and simpler catheter insertions than present guide wire methods. The advantages of enhanced sterile technique are self apparent. The measurement methods facilitated and infusion options provided by the present invention presents a vast improvement over current methods that require alternate apparatus to accomplish these same results. Although the invention has been described in detail and also described with alternate embodiments, additional embodiments exist that remain within the scope of this invention. The foregoing disclosure, descriptions and figures are only for illustrative purposes and do not, in any way, limit the invention which is defined by the following claims.

What is claimed is:

1. An apparatus for inserting and advancing a catheter, the apparatus comprising:
   a long catheter;
   an outer coating around the catheter, wherein the coating is separable from the catheter; and
   a Y-shaped housing with an entrance leading to a coating exit and a catheter exit, the housing configured to only separate the coating and the catheter such that as the coating is drawn through the housing, the coating will exit through the coating exit, and the catheter will exit through the catheter exit, thereby separating the coating from the catheter, wherein an interior of the Y-shaped housing is enclosed and includes means for separating the coating from the catheter, and wherein each of the entrance, coating exit and catheter exit has a seal attached thereto, the seals acting between the housing and the coating and the catheter.

2. The apparatus of claim 1, wherein the coating has an exterior shape that is oval, shaped or grooved, and wherein the entrance of the Y-shaped housing is correspondingly oval, shaped or grooved.

3. An apparatus for inserting and advancing a catheter, the apparatus comprising:
   a long catheter;
   an outer coating around the catheter, wherein the coating is separable from the catheter; and
   a Y-shaped housing with an entrance leading to a coating exit and a catheter exit, the housing configured to only separate the coating and the catheter such that as the coating is drawn through the housing, the coating will exit through the coating exit, and the catheter will exit through the catheter exit, thereby separating the coating from the catheter,
   wherein each of the entrance, coating exit and catheter exit has a seal attached thereto, the seals acting between the housing and the coating and the catheter, and wherein the seals define holding structure that secures the catheter when the catheter is not being advanced.

4. The apparatus of claim 1 further comprising:
   a connector attached to a distal end of the coating and attachable to an ultrasound wand.

5. The apparatus of claim 1 further comprising:
   an electric conduit contained within the outer coating to facilitate communication with at least one corresponding electric conduit within the inserted catheter to verify catheter placement.

6. An apparatus for inserting and advancing a catheter, the apparatus comprising:
   a long catheter;
   an outer coating around the catheter, wherein the coating is separable from the catheter;
   a Y-shaped housing with an entrance leading to a coating exit and a catheter exit, the housing configured to only separate the coating and the catheter such that as the coating is drawn through the housing, the coating will exit through the coating exit, and the catheter will exit through the catheter exit, thereby separating the coating from the catheter, wherein an interior of the Y-shaped housing is enclosed and includes means for separating the coating from the catheter; and
   a take-up device attachable to the coating at the coating exit of the Y-shaped housing, the take up device configured to propel the inserting catheter by drawing on the coating.

7. The apparatus of claim 1 further comprising:
   two sets of indicia, one ascending and one descending from a proximal end of the coating to a distal end, the indicia including a scale to indicate catheter insertion depth and remaining catheter length, respectively, when read at the coating exit of the Y-shaped housing.

8. The apparatus of claim 1 wherein the coating is constructed to be relatively flexible and pliant in relation to the catheter.

9. The apparatus of claim 8 further comprising:
   a slit that runs along a length of the coating, the slit extending from an outer surface of the coating through to an inner surface of the coating, wherein the slit is configured to facilitate separation of the coating from the catheter as the coating and the catheter pass through the Y-shaped housing by allowing the coating to be pulled or peeled away and to exit at an angle through the coating exit while the catheter exits through the catheter exit.

10. The apparatus of claim 8, wherein the separating means comprises:
    a knife edge positioned within the Y-shaped housing such that the knife edge will slit the coating longitudinally without slitting the catheter as the coating and catheter pass the knife edge, the knife edge configured to separate the coating from the catheter as the coating and the catheter pass through the Y-shaped housing by allowing the coating to be pulled or peeled away and exit through the coating exit while the catheter exits through the catheter exit.

11. The apparatus of claim 8 further comprising:
    a cutting wire disposed between the catheter and the coating such that the wire will slit the coating longitudinally as the coating moves through the Y-shaped housing, thereby causing the coating to peel away from the catheter and exit through the coating exit while the separated catheter exits through the catheter exit of the Y-shaped housing.

12. The apparatus of claim 8 wherein:
    a strip of the coating extending longitudinally along the length of the coating comprises a lesser thickness than the rest of the coating, the strip allowing the coating to separate from the catheter as the catheter and coating move through the Y-shaped housing such that the coating will exit through the coating exit, and the catheter will exit through the catheter exit.

13. The apparatus of claim 8 further comprising:
a band of material attached along the length of the catheter, the band separating from the catheter when the band moves at an angle through the coating exit of the Y-shaped housing, thereby propelling the catheter through the catheter exit.

* * * * *